United States Patent [19]

Gunderson

[11] Patent Number: 5,330,508
[45] Date of Patent: Jul. 19, 1994

[54] APPARATUS FOR DETECTION AND TREATMENT OF TACHYCARDIA AND FIBRILLATION

[75] Inventor: Bruce Gunderson, Plymouth, Minn.

[73] Assignee: Medtronic, Inc., Minneapolis, Minn.

[21] Appl. No.: 24,996

[22] Filed: Mar. 2, 1993

[51] Int. Cl.$^5$ .................. A61N 1/362; A61B 5/0464
[52] U.S. Cl. ...................... 607/14; 128/705; 364/413.06
[58] Field of Search .............. 128/705, 706, 702; 607/14, 25; 364/413.06

[56] References Cited

U.S. PATENT DOCUMENTS

| | | | |
|---|---|---|---|
| 3,820,025 | 6/1974 | Lahr et al. | 128/706 |
| 4,375,817 | 3/1983 | Engle . | |
| 4,385,585 | 5/1983 | Zipes . | |
| 4,548,209 | 10/1985 | Wielders . | |
| 4,587,970 | 5/1986 | Holley . | |
| 4,693,253 | 9/1987 | Adams . | |
| 4,726,380 | 2/1988 | Vollmann . | |
| 4,819,643 | 4/1989 | Menken . | |
| 4,830,006 | 5/1989 | Haluska . | |
| 4,880,004 | 11/1989 | Baker, Jr. . | |
| 4,880,005 | 11/1989 | Pless . | |
| 4,949,719 | 8/1990 | Pless . | |
| 4,949,730 | 8/1990 | Cobben . | |
| 4,953,551 | 9/1990 | Mehra . | |
| 4,969,465 | 11/1990 | Pless et al. | 607/14 |
| 4,971,058 | 11/1990 | Pless . | |
| 5,116,824 | 5/1992 | Miyata . | |
| 5,163,427 | 11/1992 | Keimel . | |

OTHER PUBLICATIONS

"Reliable R-Wave Detection From Ambulatory Subjects", by Thakor, Biomed Sci. Instrum. 14:67-72, 1978.
"Onset and Stability for Ventricular Tachyarrhythmia Detection in an Implantable Pacer-Cardioverter-Defibrillator", by Walter H. Olson, et al., Computers in Cardioloby, Oct. 7-10, 1986.

Primary Examiner—William E. Kamm
Assistant Examiner—Kennedy J. Schaetzle
Attorney, Agent, or Firm—Reed A. Duthler; Harold R. Patton

[57] ABSTRACT

An implantable cardioverter/defibrillator provided with method and apparatus for discrimination between tachycardia and fibrillation. The device is measures the interval separating depolarization of the heart, sorts the measured interval into interval ranges, counts the number of intervals in each range, and, based on the distribution of intervals within the rate ranges, identifies tachycardia or fibrillation. In its preferred embodiment, the device triggers delivery of therapies appropriate for treatment of tachycardia and fibrillation.

16 Claims, 7 Drawing Sheets

APPARATUS FOR DETECTION AND TREATMENT OF TACHYCARDIA AND FIBRILLATION

BACKGROUND OF THE INVENTION

This invention relates to devices which detect and/or treat tachyarrhythmias (rapid heart rhythms), and more specifically, to mechanisms to distinguish among various tachyarrhythmias and to provide appropriate therapies to treat the identified tachyarrhythmias.

Early automatic tachyarrhythmia detection systems for automatic cardioverter/defibrillators relied upon the presence or absence of electrical and mechanical heart activity (such as intramyocardial pressure, blood pressure, impedance, stroke volume or heart movement) and/or the rate of the electrocardiogram to detect hemodynamically compromising ventricular tachycardia or fibrillation.

In pacemaker/cardioverter/defibrillators presently in clinical evaluation, fibrillation is distinguished from ventricular tachycardia using rate based criteria, In such devices, it is common to specify the rate or interval ranges that characterize a tachyarrhythmia as opposed to fibrillation. However, some patients may suffer from ventricular tachycardia and ventricular fibrillation which have similar or overlapping rates, making it difficult to distinguish low rate fibrillation from high rate tachycardia. In addition, ventricular fibrillation may display R-R intervals which may vary considerably, resulting in intervals that may fall within both the tachycardia and fibrillation rate or interval ranges, or outside both.

Presently available pacemaker/cardioverter/defibrillator arrhythmia control devices, such as the Model 7216 and Model 7217 devices commercially available from Medtronic, Inc., employ programmable fibrillation interval ranges and tachycardia detection interval ranges which are adjacent to one another. In the Medtronic devices in particular, the interval range designated as indicative of fibrillation consists of intervals less than a programmable interval (FDI) and the interval range designated as indicative of ventricular tachycardia consists of intervals less than a programmable interval (TDI) and greater than or equal to FDI. R-R intervals falling within these ranges are measured and counted to provide a count (VTEC) of R-R intervals falling within the tachycardia interval range and a count (VFEC) of the number of intervals which fall within the fibrillation interval range, out of a preceding series of a predetermined number (FEB) of intervals. VTEC is incremented in response to R-R intervals that are greater than or equal to FDI but shorter than TDI, is reset to zero in response to intervals greater than or equal to TDI and is insensitive to intervals less than FDI. VTEC is compared to a programmed value (VTNID) and VFEC is compared to a corresponding programmable value (VFNID). When one of the counts equals its corresponding programmable value, the device diagnoses the presence of the corresponding arrhythmia, i.e. fibrillation or tachycardia and delivers an appropriate therapy, e.g. anti-tachycardia pacing, a cardioversion pulse or a defibrillation pulse. In addition, the physician may optionally require that the measured R-R intervals meet a rapid onset criterion before VTEC can be incremented and can also optionally require that should a rate stability criterion fail to be met, VTEC will be reset to zero. This detection system has proven effective in distinguishing between fibrillation and ventricular tachycardia so that appropriate therapies may be delivered. However, an increased level of accuracy in classifying rhythms having intervals close to FDI is believed desirable. In addition, the ability to provide a separate therapy set for fast tachycardias as opposed to slower tachycardias is also desirable.

SUMMARY OF THE INVENTION

In a general sense, one object of the present invention is to distinguish between a tachycardia occurring in a chamber of a heart (e.g. ventricular tachycardia) from rhythms of a similar average rate, but occurring due to a different cause. A second, corresponding object is thus to accurately deliver antiarrhythmia therapies to treat the identified tachyarrhythmias.

In one disclosed embodiment, the present invention is employed to accurately distinguish fibrillation from fast tachycardias at similar rates. In a second disclosed embodiment, the present invention is employed to distinguish ventricular tachycardia from a rapid ventricular rhythm due to atrial fibrillation. In its preferred embodiments, the device takes the form of an implantable pacemaker/cardioverter/defibrillator, and the invention in these embodiments also provides therapies appropriate to the detected tachyarrhythmia. The disclosed embodiments sense the rhythm of the ventricle and provide therapy for the ventricle, but the invention is also believed to be of value in detecting and treating atrial fibrillation and tachycardias.

In accordance with the present invention, it is realized that because of the randomness of sensed intervals between depolarizations during fibrillation or because of uncertainties related to a patient's rhythms, sensed cardiac depolarization intervals during fibrillation may have durations which overlap those observed during tachycardias. From the perspective of a device which diagnoses arrhythmias based on measured intervals or rates, intervals or rates defined as indicative of tachycardia, for example, may in fact be occurring during fibrillation. The present invention in this circumstance provides a method and apparatus for quickly and accurately classifying the nature of a tachyarrhythmia with intervals near the border between the interval or rate ranges associated with tachycardia and fibrillation.

Similarly, ventricular rhythms which may occur due to atrial fibrillation may display an average rate which would may overlap with the rates seen during ventricular tachycardia, but generally display substantially more variability of R-R interval duration. In this circumstance, the invention provides a method accurately determining whether the sensed rhythm is a treatable ventricular tachycardia and of avoiding the ineffective delivery of therapies if the rapid rhythm is due to atrial fibrillation, The disclosed embodiments of the invention operate in the ventricle of the heart and accomplish identification of such rhythms using a methodology which provisionally detects ventricular tachycardia and/or fibrillation and thereafter applies a discrimination function to the series of measured intervals preceding the provisional detection. Discrimination is accomplished by sorting the intervals preceding provisional detection into bins corresponding to interval ranges and examining the relative distribution of the intervals, within the bins. In the specific embodiments enclosed, a predetermined number of intervals are binned, and a determination is made of whether there exists a predetermined number of bins (e.g. two bins), within a designated set of bins, which have a total number of at least a predetermined threshold number of intervals (e.g. 14 intervals), out of a preceding series of a predetermined number of intervals (e.g. 18 intervals). If so, the discrimination criterion is met.

In the disclosed embodiment in which the invention is used to distinguish between fast VT and VF, if the discriminator criterion is met, the rhythm is determined to be a fast ventricular tachycardia, and a fast tachycardia therapy (e.g. cardioversion or antitachycardia pacing) is delivered. If the criterion is not met, the discrimination criterion is not met, the rhythm is determined to be fibrillation and a fibrillation therapy (e.g. a defibrillation pulse) is delivered.

In the disclosed embodiment in which the invention is used to distinguish between VT and fast ventricular rhythms due to atrial fibrillation, if the discriminator criterion is met, the rhythm is determined to be a ventricular tachycardia, and a tachycardia therapy (e.g. cardioversion or antitachycardia pacing) is delivered. If the criterion is not met, the discrimination criterion is not met, the rhythm is determined to be due to atrial fibrillation and no therapy is delivered.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which.

DETAILED DESCRIPTION OF THE PREFERRED EMBODIMENTS

Figure 1:
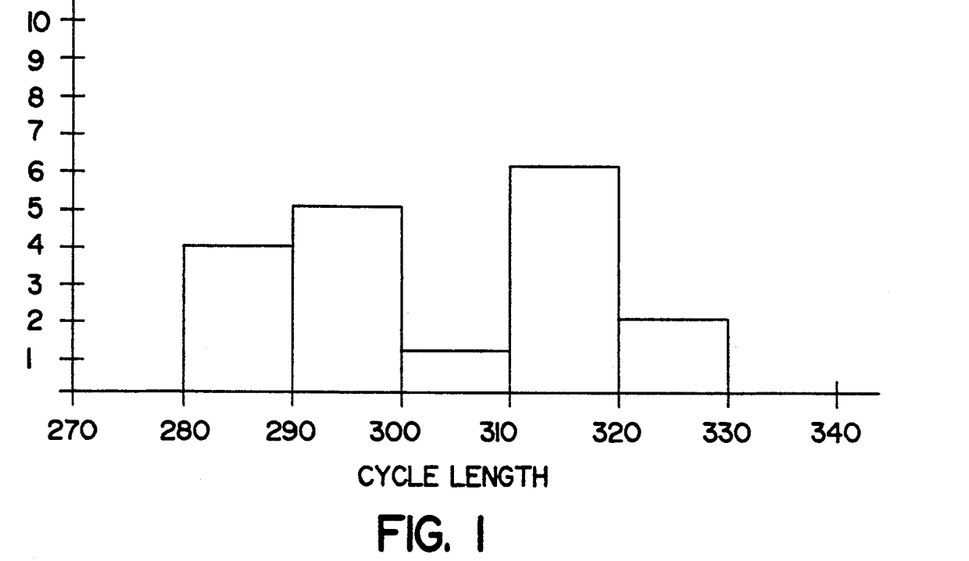
FIG. 1 is an illustration of binned intervals associated with fibrillation.

FIG. 1 illustrates intervals falling within a set of bins, each bin being 10 ms in width. The binned intervals illustrated occurred during an episode of ventricular fibrillation. The 18 intervals preceding initial detection of fibrillation have an average duration of 300-310 milliseconds. An examination of the binned intervals reveals that the two intervals bins with the highest values (290-300, 310-320) include 11 total binned intervals.

Figure 2:
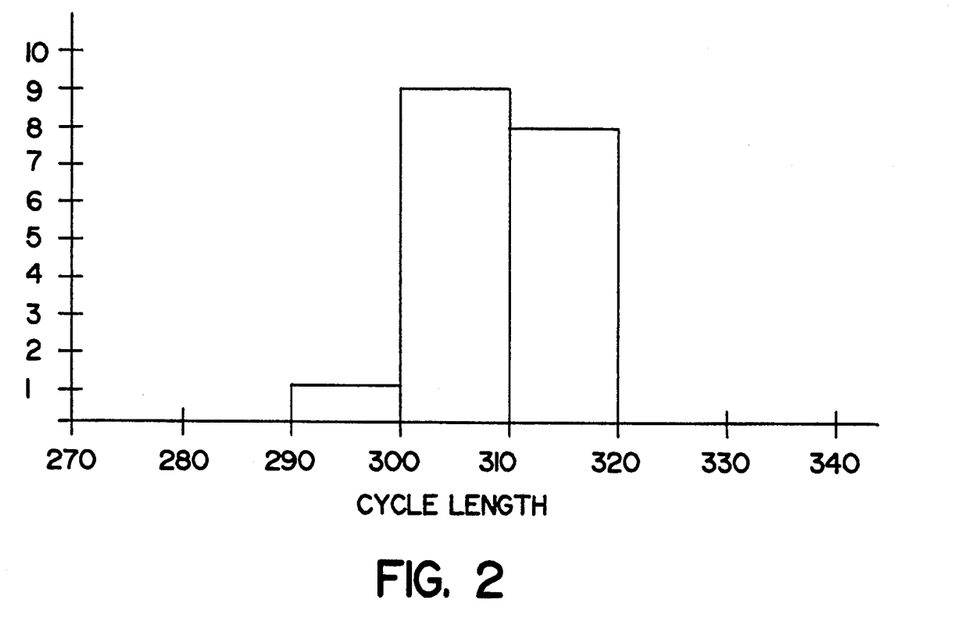
FIG. 2 is an illustration of binned intervals associated with tachycardia.

FIG. 2 illustrates a set of binned intervals obtained during high rate tachycardia, having an average interval length approximately the same as the fibrillation illustrated in FIG. 1. However, 17 out of 18 of the binned intervals fall within two bins. This difference in the distribution of intervals within the bins can be employed to distinguish high rate monomorphic ventricular tachycardia from fibrillation, occurring at similar rates. For example, a requirement that 14 out of the 18 binned intervals preceding initial detection of fibrillation fall within two bins within a designated set of bins corresponding to interval ranges greater than a preset value may serve as a mechanism for detecting that the sensed rhythm was ventricular tachycardia, rather than fibrillation.

In the context of the first embodiment of the present invention, it is suggested that this discrimination function is applied in response to a provisional detection of ventricular fibrillation. In order to avoid erroneously meeting the discrimination criterion in response to high rate fibrillation, it is recommended that only interval bins corresponding to interval ranges greater than a predetermined interval FTDI (e.g. 240 ms) be considered in determining whether the discriminator criterion is met. The interval ranges, the numbers of bins, the numbers of intervals and the other parameters of the discriminator function may be programmable by the physician. However, it is believed that for most patients, the specific set of parameters set forth below will serve to distinguish VF from VT, and as such could be employed in a device having preset parameters for the discrimination function, substantially simplifying the physician's task in using the device.

In the first embodiment disclosed below, the discrimination function is activated in response to detection of a rhythm which could be either ventricular fibrillation or fast ventricular tachycardia. The particular embodiment disclosed accomplishes this provisional detection function, using a modified version of the detection methodology employed in the Medtronic 7216 and Medtronic 7217 implantable pacemaker/cardioverter/defibrillators. However, the present invention is believed to be useful in the context of any device capable of detecting an arrhythmia which is not unambiguously identified as either tachycardia or fibrillation. Thus, the present invention is believed readily incorporated in devices having basic detection methodologies similar to any of those disclosed in the prior art, and should be considered in this context when reviewing the specific embodiments discussed below.

Figure 3:
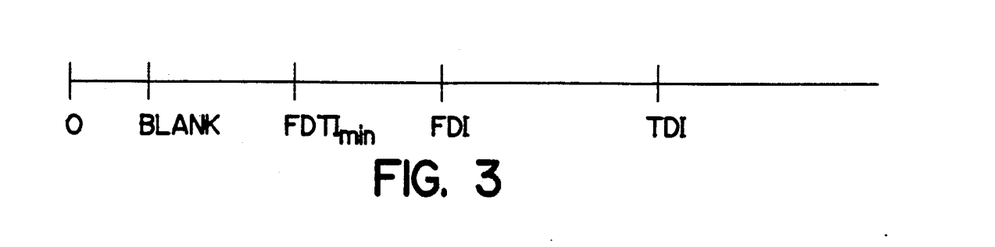
FIG. 3 is an illustration of the defined intervals employed in the first preferred embodiment of the present invention.

FIG. 3 is an illustration of the rate ranges which are employed in the first preferred embodiment of the present invention. The range of intervals which are taken as indicative of sinus rhythm includes those which are greater than or equal to TDI. The range of intervals taken as indicative of tachycardia includes intervals less than TDI, but greater than or equal to FDI. The range of intervals taken as indicative of fibrillation includes intervals less than FDI and greater than or equal to the blanking interval. If ventricular fibrillation is provisionally detected, bins corresponding to intervals greater than or equal to FTDI are examined and are employed in the discrimination function.

In the first embodiment of the invention discussed below, using interval ranges corresponding to FIG. 3, the tachycardia and fibrillation detection criteria discussed above in conjunction with the Medtronic Model 7216 and Model 7217 implantable pacemaker/cardioverter/defibrillators are retained, and used as one set of criteria for provisional detection of tachycardia or fibrillation. In addition to the fibrillation and tachycardia detection criteria discussed above in connection with the Medtronic Model 7216 and Model 7217, (i.e. VFEC=VFNID or VTEC=VTNID), provisional detection of tachycardia or fibrillation detection may also be accomplished using a combined count of all intervals indicative of tachycardia or fibrillation. This combined count (VFEC+VTEC) is compared to a combined count threshold (CNID). If VTEC+VFEC is equal or greater than CNID, the device checks to see whether VFEC is at least a predetermined number (e.g. 6). If so, the device checks to determine how many of a number (e.g. 8) of the immediately preceding intervals are greater or equal to FDI. If a predetermined number (e.g. 8) are greater than or equal to FDI, tachycardia is provisionally detected, otherwise ventricular fibrillation is provisionally detected. The immediately preceding measured intervals are then examined as discussed below to determine whether the provisional detection of fibrillation should be confirmed or amended to indicate detection of fast ventricular tachycardia.

Figure 6:
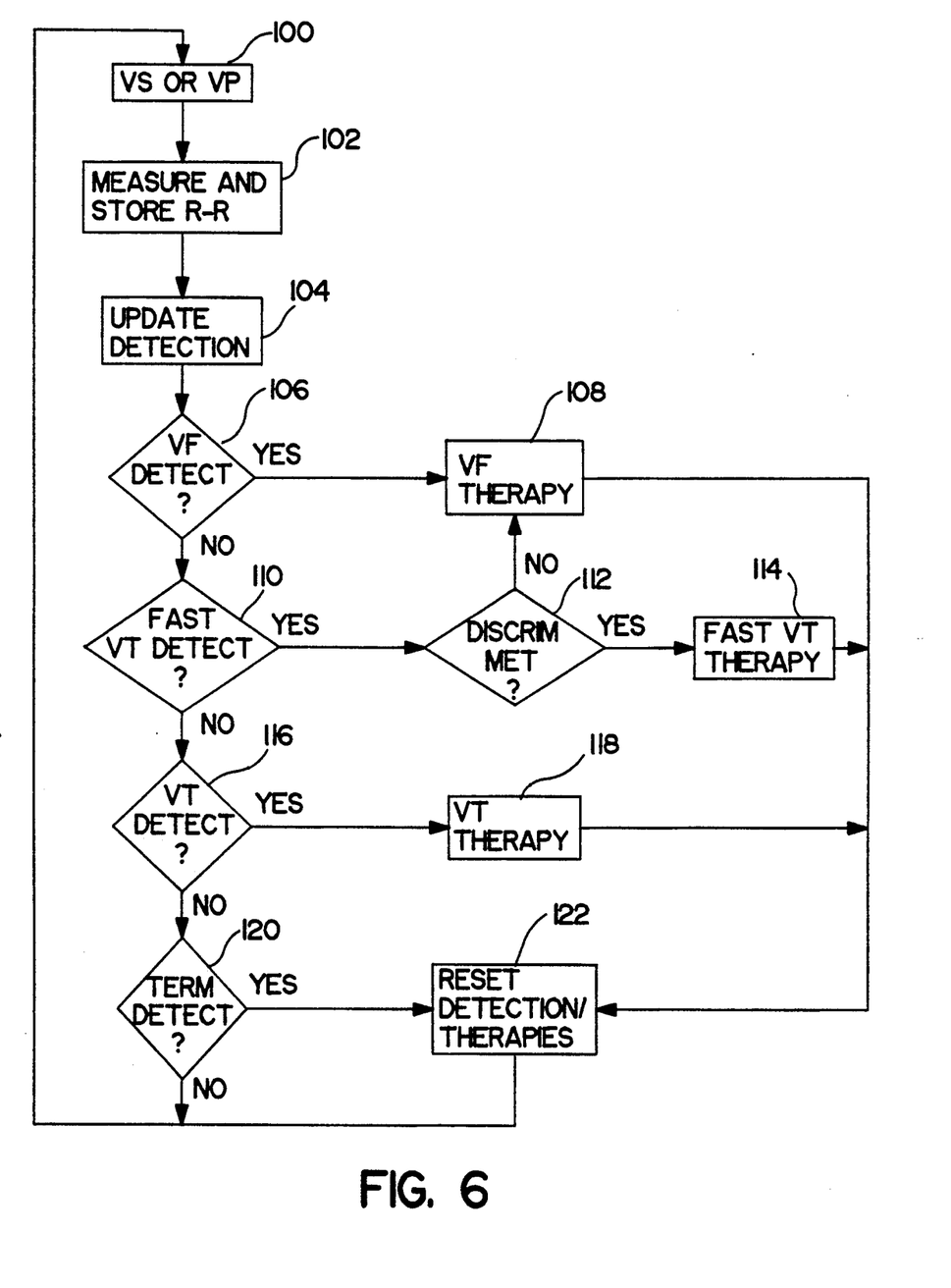
FIG. 6 is a simplified flow chart diagram illustrating the functional operation of a second preferred embodiment of the present invention.

The present invention, in the first preferred embodiment, is practiced by adding specific new features to the underlying detection methodology of existing prior devices. However, the value of the present invention is not limited to the context of the specific detection criteria disclosed, but is believed workable and valuable in the context of any devices which distinguish between tachycardia and fibrillation using rate or interval based criteria. For example, FIG. 6 illustrates an alternative method of employing the present invention to distinguish between VF and fast VT.

Figure 4:
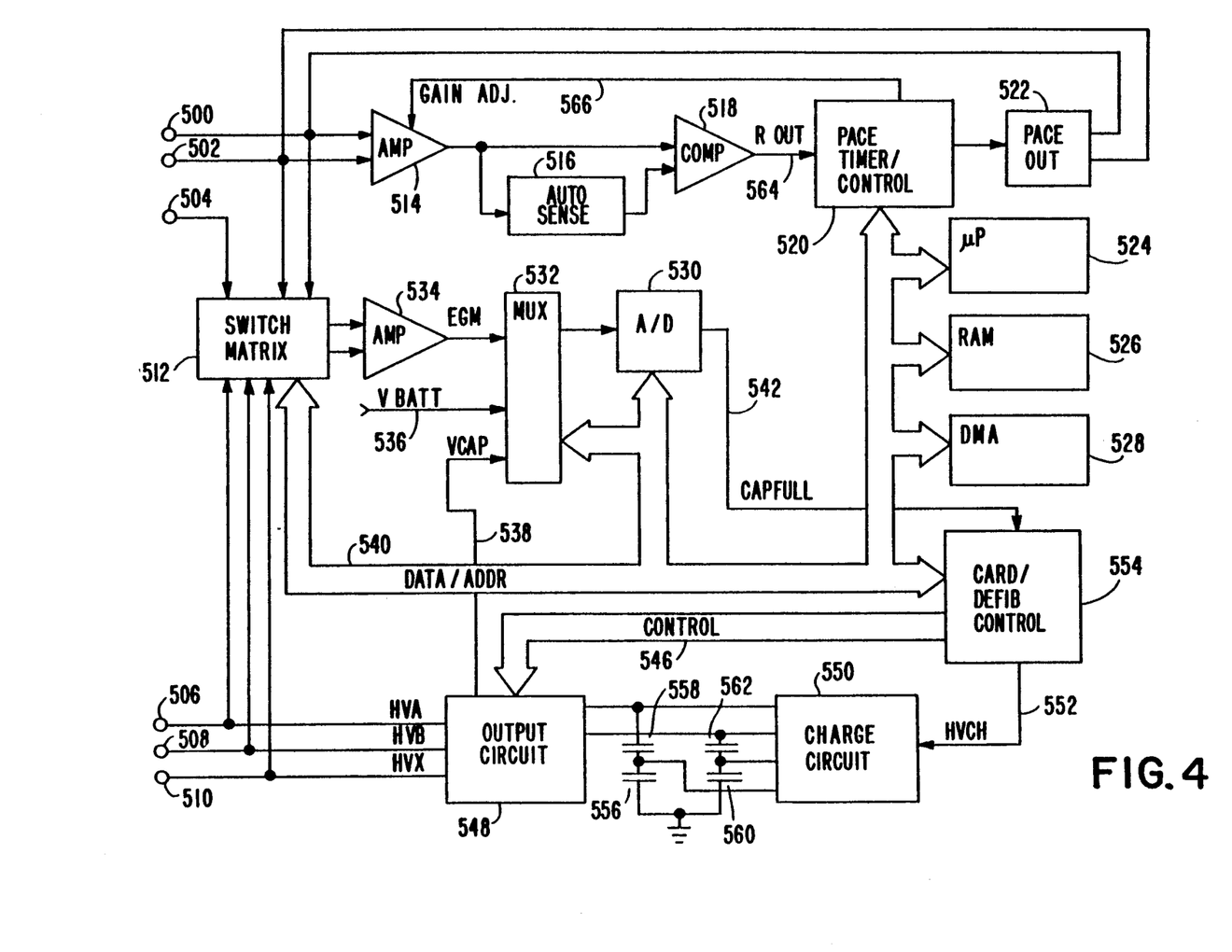
FIG. 4 is a simplified block diagram illustrating the components of a device within which the method and apparatus of the present invention may be implemented.

FIG. 4 is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/defibrillators as disclosed in prior U.S. Pat. No. 4,548,209, issued to Wielders, et. al. on Oct. 22, 1985, U.S. Pat. No. 4,693,253, issued to Adams et. al. on Sep. 15, 1987, U.S. Pat. No. 4,830,006, issued to Haluska et. al. on May 6, 1989 and U.S. Pat. No. 4,949,730, issued to Pless et. al. on Aug. 21, 1990, all of which are incorporated herein by reference in their entireties.

The device is illustrated as being provided with six electrodes, 500, 502, 504, 506, 508 and 510. Electrodes 500 and 502 may be a pair of endocardial electrodes located in the ventricle, mounted to a transvenous lead. Electrode 504 may correspond to a remote, indifferent electrode located on the housing of the implantable pacemaker/cardioverter/defibrillator. Electrodes 506, 508 and 510 may correspond to the large surface area defibrillation electrodes located on ventricular, coronary sinus, superior vena cava or subcutaneous leads, to electrodes located on or part of the device housing or to epicardial defibrillation electrodes.

Electrodes 500 and 502 are shown as hard-wired to the R-wave detector circuit, comprising band-pass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by the auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned U.S. Pat. No. 5,118,824, issued to Keimel and incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present invention.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp. 67-72, 1978, incorporated herein by reference in its entirety. The invention may also be practiced in conjunction with more traditional R-wave sensors of the type comprising a band pass amplifier and a comparator circuit to determine when the bandpassed signal exceeds a predetermined, fixed sensing threshold.

Switch matrix 512 is used to select which of the available electrodes are coupled to band pass amplifier 534. Selection of which two electrodes are so coupled is controlled by the microprocessor 524 via data/address bus 540. Signals from the selected electrodes are passed through band-pass amplifier 534 and into multiplexer 532, where they are converted to multi-bit digital signals by A/D converter 530, for storage in random access memory 526 under control of direct memory address circuit 528. Microprocessor 524 analyzes the digitized EGM signal stored in random access memory 526 to determine the width of the stored R-wave or in conjunction with the tachycardia/fibrillation discrimination function discussed below.

Amplifier 534 may be a broad band pass amplifier, having a band pass extending for approximately 0.5 to 200 hertz. The filtered EGM signal from amplifier 534 is passed through multiplexer 532, and digitized in A-D converter circuitry 530. The digitized EGM data is stored in random access memory 526 under control of direct memory address circuitry 528. Preferably, a portion of random access memory 526 is configured as a looping or buffer memory which stores at least the preceding several seconds of the EGM signal.

The occurrence of an R-wave detect signal on line 564 in communicated to microprocessor 524 via data/address bus 540, and microprocessor 524 notes the time of its occurrence, calculates the R-R interval and stores it for later reference. The stored R-R intervals may be stored in a buffer memory so that only the most recent series of intervals are stored, in the same fashion as the ECG. The microprocessor also updates counts related to the R-R intervals previously sensed. The counts, VFEC and VTEC, are incremented on the occurrence of a measured R-R intervals falling within the fibrillation and ventricular tachycardia ranges, respectively, as discussed above. These rate ranges may be defined by the programming stored in the RAM 526.

These counts, along with other stored information reflective of the previous series of R-R intervals such as information regarding the rapidity of onset of the detected short R-R intervals, the stability of the detected R-R intervals, the duration of continued detection of short R-R intervals, the average R-R interval duration and information derived from analysis of stored EGM segments are used to determine whether tachyarrhythmias are present and to distinguish between different types of tachyarrhythmias, as discussed above in conjunction with FIG. 3. Other such detection algorithms for recognizing tachycardias are described in the above cited U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated by reference in its entirety herein. However, other criteria may also be measured and employed in conjunction with the present invention.

It is envisioned that onset and stability requirement are optional in a device employing the present invention, and preferably are made available as programmable options, which may be deleted by external programmer command. If included, it is believed preferable that the onset criteria be required to met prior to initiating counting of VTEC, and that once met, the criterion will remain satisfied until detection of tachycardia termination. Thus, onset is not intended to be a detection criteria required for re-detection of tachycardia, following initial detection. The width criterion, if used, should also be understood to preferably used only in initial detection of tachycardia. This reflects a presumption that following initial detection of ventricular tachycardia, absent a proven return to normal heart rhythm (termination detect), subsequent high ventricular rates should be presumed to be ventricular in origin. The stability criterion, on the other hand, is believed to be appropriate for use both in initial detection of tachycardia and in re-detection of tachycardia.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of band-pass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R-R intervals, to detect the presence of tachycardia and to determine whether the minimum rate criteria are met for activation of the width measurement function.

Microprocessor 524 operates as an interrupt driven device, and responds to interrupts from pacer timing-/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an antitachyarrhythmia pacing regimen is desired, appropriate timing intervals for controlling generation of anti-tachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the even that generation of a cardioversion or defibrillation pulse is required, microprocessor 524 employs the counters in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in allowed, commonly assigned U.S. patent application Ser. No. 07/612,761, by Keimel, for an Apparatus for Detecting and Treating a Tachyarrhythmia, filed Nov. 15, 1990 and incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24, 1983, in U.S. Pat. No. 4,949,719 issued to Pless et al., cited above, and in U.S. Pat. No. 4,375,817, issued to Engle et al., all incorporated herein by reference in their entireties may also be employed. Similarly, known circuitry for controlling the timing and generation of anti-tachycardia pacing pulses as described in U.S. Pat.

No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In modern pacemaker/cardioverter/defibrillators, the particular antitachycardia and defibrillation therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Prior art patents illustrating such pre-set therapy menus of antitachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et el. The present invention is believed practicable in conjunction with any of the known anti-tachycardia pacing and cardioversion therapies, and it is believed most likely that the invention of the present application will be practiced in conjunction with a device in which the choice and order of delivered therapies is programmable by the physician, as in current implantable pacemaker/cardioverter/defibrillators.

In addition to varying the therapy delivered following a failed attempt to terminate a tachyarrhythmia, it is also known that adjustment of detection criteria may be appropriate. For example, adjustment may comprise reducing the number of intervals required to detect a tachyarrhythmia to allow a more rapid redetection or by changing the interval ranges to bias detection towards detection of ventricular fibrillation, for example as disclosed in U.S. Pat. No. 4,971,058, issued to Pless et al and incorporated herein by reference in its entirety.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in U.S. Pat. No. 5,163,427, issued to Keimel, incorporated herein by reference in its entirety. However, output control circuitry as disclosed in U.S. Pat. No. 4,953,551, issued to Mehra et. al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

Figure 5A:
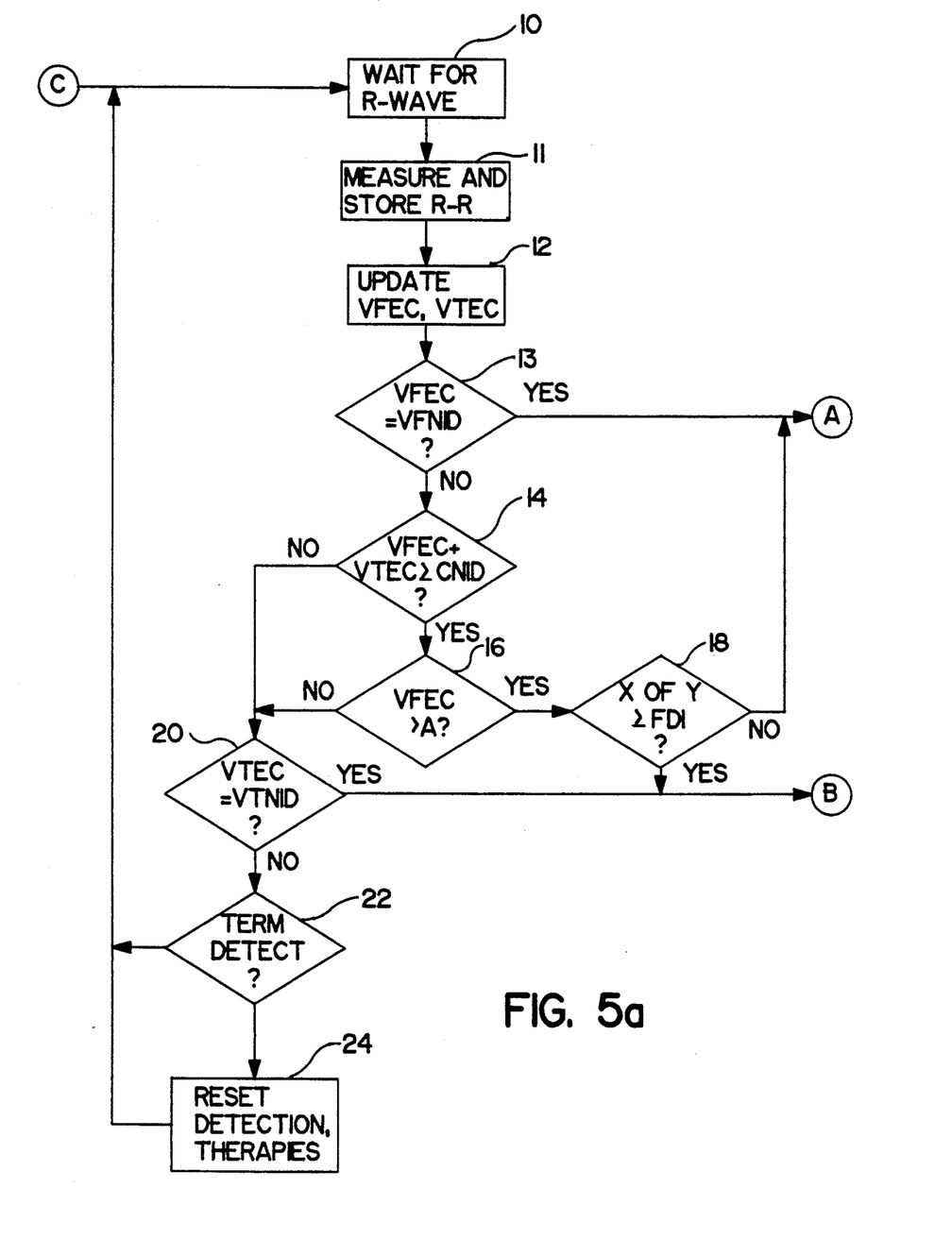
FIGS. 5a, 5b and 5c are simplified flow chart diagrams illustrating the functional operation of a first preferred embodiment of the present invention.
Figure 5B:
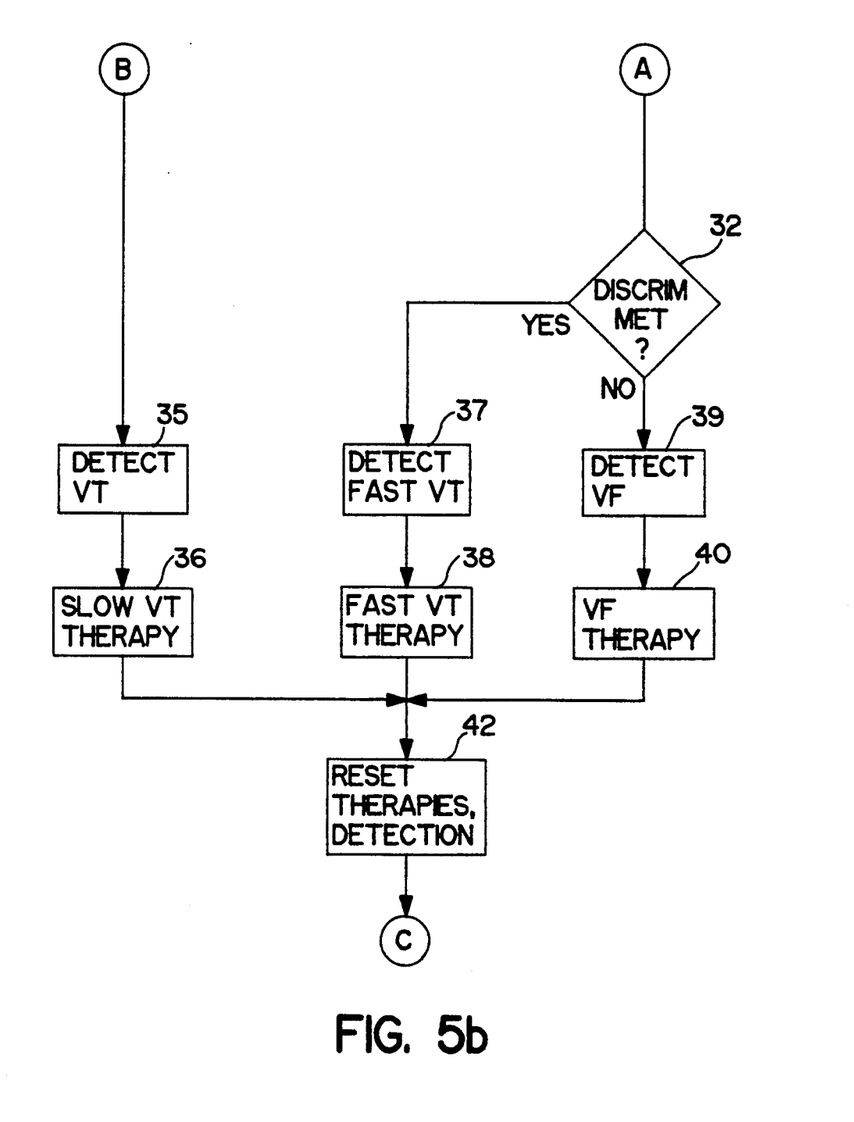
Figure 5C:
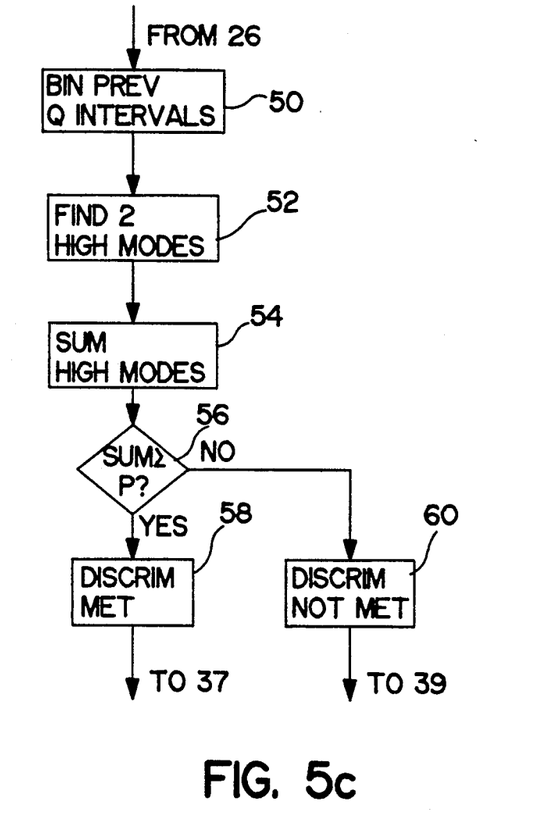

FIGS. 5a, 5b and 5c are a functional flow chart illustrating the operation of the first preferred embodiment of the present invention, as embodied in the context of a device illustrated in FIG. 2. In FIG. 5a, it should be understood that the device may be in general operating as a demand pacemaker, and that the analysis undertaken takes place in response to the occurrence of sensed or paced depolarizations of the heart. At 10, the device is awaiting the occurrence of the next subsequent R-wave. Upon occurrence of the R-wave, the process and functions described above related to storing the time of occurrence of the R-wave, measuring and storing the R-R interval preceding the R-wave are performed at 11. At 12, the VTEC and VFEC counts are updated.

At 13, device checks to determine whether VFEC equals VFNID. If so, fibrillation is provisionally detected. If not, the sum of VFEC and VTEC is compared to CNID at 14. If their sum is equal to or greater than CNID, the device checks at 16 to determine whether VFEC is greater than a predetermined number, for example 5. If so, the device checks at 18 to see whether a predetermined number X of the preceding Y R-R intervals (e.g. at least 7 or all 8 out of the preceding 8 intervals) are greater than or equal to FDI. If so, tachycardia is provisionally detected, if not, fibrillation is provisionally detected.

In the event that either the sum of VFEC+VTEC is less than CNID at 14 or VFEC is less than or equal to A at 16, the device checks at 20 to determine whether VTEC equals VTNID. If so, ventricular tachycardia is detected, if not, the device checks at 22 to determine whether a tachyarrhythmia has previously been detected and whether the previous series of R-waves indicate termination of the previously detected tachyarrhythmia. Detection of termination of tachycardia or fibrillation may be accomplished by means of detection of a predetermined number (e.g. 8) of sequential R-R intervals indicative of normal heart rate. Normal heart rate may be defined as R-R intervals greater than or equal to TDI. If termination is detected, detection criteria and anti-arrhythmia therapy menus are reset at 24, as described above in conjunction with FIG. 4. If not, the device simply waits for the next R-wave at 10.

In the event that tachycardia is provisionally detected at 18 or 20, the device simply proceeds to detect slow VT at 35 (FIG. 5b) and to deliver slow VT therapy at 36. In the event that fibrillation is provisionally detected at 13 or 18, the device checks at 32 (FIG. 5b) to determine whether the discrimination criterion is met. If the criterion is not met, ventricular fibrillation is detected at 39 and fibrillation therapy is delivered at 40. If the criterion is met, fast ventricular tachycardia is detected at 37 and fast VT therapy is delivered at 38. After delivery of therapy at 36, 38 or 40 or following inhibition of anti-tachycardia therapy at 34, the therapy menus and detection criteria are reset at 42 to reflect the preceding detection of tachyarrhythmia and delivery of tachyarrhythmia therapy, as discussed above in conjunction with FIG. 4. The device then returns to block 10, awaiting the next successive R-wave, so that it may determine whether the tachyarrhythmia has been terminated, persists, or has changed to another type of tachyarrhythmia.

FIG. 5c illustrates the discrimination function in more detail, and corresponds to block 32 of FIG. 5b. At 50, the microprocessor reads the most recent 18 stored intervals and sorts them into corresponding interval ranges or bins as illustrated in FIGS. 1 and 2. For purposes of the present embodiment, interval ranges or bins 10 ms in width are believed workable, although other bin widths may be employed. At 52, the microprocessor determines which two bins having interval ranges greater than FTDI (240 ms) hold the greatest numbers of intervals and at 54 the numbers of intervals in the two identified bins are summed. At 56, the sum is to determine whether it is greater than or equal to 14. If so, the discrimination criterion is considered to be met at 58. If not, the criterion is considered not to be met at 60.

As discussed above, while the parameters described above are believed workable with most patients, other parameters may be employed. For example, if bins having widths of less than 10 ms are employed, the threshold number may be compared to the summed counts in three or more bins. Similarly, the number of preceding intervals binned and the threshold number of intervals may also be varied, as can the value of FTDI.

FIG. 6 is a functional flow chart illustrating a more general application of the present invention in the context of an implantable pacemaker/cardioverter/defibrillator, of the type generally illustrated and described in conjunction with FIG. 4, but not employing the specific methodologies for provisional detection of arrhythmias set forth above. At 100, the device awaits the occurrence of a ventricular depolarization, sensed or paced. At 102, the device measures and stores the preceding R-R interval and at 104, updates its detection methodology. For purposes of FIG. 6, it should be understood that the device may employ an interval based detection methodology as described above, or may employ a rate-based detection methodology, depending upon the average rate, or depending upon a mixture of average rate and intervals, as disclosed in the Pless et. al. U.S. Pat. No. 4,969,465, cited above. At 104 the device checks to see whether criteria for provisional detection of ventricular fibrillation are met. If so, a defibrillation pulse is generated at 108, the detection and therapy menus are reset at 122 and the device returns to bradycardia pacing, awaiting the next paced or sensed ventricular event.

In the event that ventricular fibrillation is not unambiguously identified at 106, the device checks at 110 to determine whether a rhythm which could be either a fast ventricular tachycardia or fibrillation has occurred. In the context of devices employing multiple rate ranges, with corresponding detection criteria for each rate range, this may correspond to the provisional detection of fast ventricular tachycardia. Alternatively, this could correspond to a detection of a rhythm that overlaps rate or interval boundaries associated with provisional detection of fibrillation and ventricular tachycardia, in a system employing essentially two interval ranges. Regardless of the specific detection methodology employed, identification of a rhythm which has a rate and/or average interval consistent with either VF or VT activates the discriminator function at 112. The discriminator function corresponds to FIG. 5c, illustrated above. In the event that the discriminator criteria is not met, defibrillation is administered at 108, in the same fashion as described in conjunction with FIG. 5b above. In the event that the discrimination criteria is met, a fast ventricular tachycardia therapy is delivered at 114, and the detection and therapy menus are updated at 122.

If the device does not detect a rhythm at 110 which could be indicative of either tachycardia or fibrillation, it checks at 116 to determine whether a rhythm which is identifiable as a slower ventricular tachycardia has been detected at 116. If so, antitachycardia therapy is delivered at 118 and the detection and therapy menus are reset at 122. If not, the device checks at 120 to determine whether determination of any previously detected tachycardias or fibrillation has been detected. If so, the detection and therapy menus are reset at 122, if not, the device continues to function as a VVI pacemaker, awaiting the next sensed or paced ventricular depolarization at 100.

Figure 7:
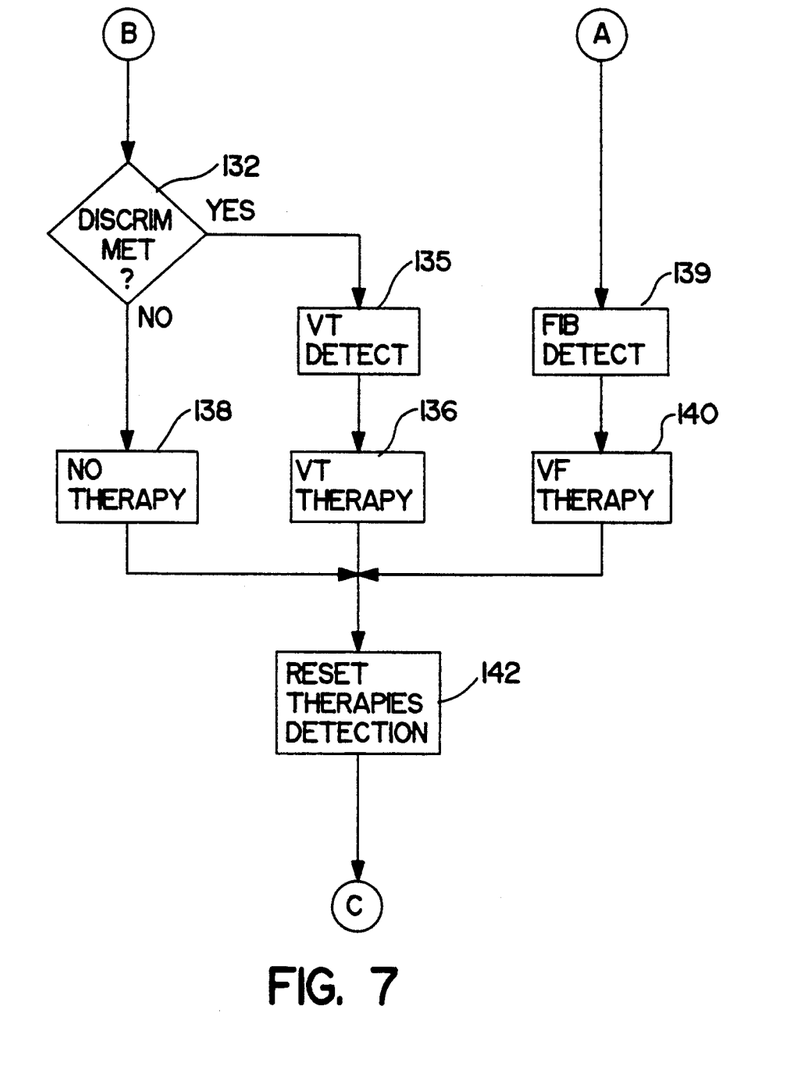
FIG. 7 is a simplified flow chart diagram illustrating the functional operation of a third preferred embodiment of the present invention.

FIG. 7 illustrates a third embodiment of the present invention in which the discrimination function is used to distinguish between VT and rapid ventricular rhythms due to atrial fibrillation. In this embodiment, provisional detection of VT activates the discriminator function. If the discriminator criterion is not met, the rhythm is presumed to be due to atrial fibrillation and no therapy is delivered. This third embodiment should be understood to be practiced in a device otherwise as described in conjunction with FIGS. 4, 5a and 5c. FIG. 7 should may be directly substituted for FIG. 5b, and the discriminator function corresponds to that illustrated in FIG. 5c.

In the event that tachycardia is detected at 18 or 20, the device checks at 132 to determine whether discrimination criterion is met. If the criterion is not met, therapy is aborted at 138. If the criterion is met, ventricular tachycardia is detected at 135 and VT therapy is delivered at 136. In the event that fibrillation is provisionally detected at 13 or 18, the device detects the occurrence of fibrillation at 139 and delivers a defibrillation pulse at 140. After delivery of therapy at 136 or 140 or following cancellation of therapy at 138 the therapy menus and detection criteria are reset at 142 to reflect the preceding detection of tachyarrhythmia and delivery of or cancellation of tachyarrhythmia therapy, as discussed above in conjunction with FIG. 4. The device then returns to block 10, (FIG. 5a), awaiting the next successive R-wave, so that it may determine whether the detected tachyarrhythmia has been terminated, persists, or has changed to another type of tachyarrhythmia.

For purposes of FIG. 7, the discriminator function at 132 corresponds to that illustrated in FIG. 5c. However, the number of intervals binned, the number of bins available to meet the threshold value and the threshold value may vary from those used when the discriminator is activated in response to a provisional detection of VF. In such a case, it is anticipated that the physician may wish to optimize the discrimination function parameters based on a physiologic work-up of the individual patient. While FIGS. 5b and 7 illustrate alternative uses of the discriminator function, it is also within the scope of the present invention to employ the discriminator function in response to both provisional detection of fibrillation and provisional detection of tachycardia. In such a case, it is anticipated that the parameters for the discriminator function may vary depending on whether tachycardia or fibrillation is provisionally detected.

While the preferred embodiment of the device takes the form of a microprocessor controlled device as illustrated in FIG. 4, in which the various functional steps illustrated in FIGS. 5a, 5b, 5c, 6 and 7 would be implemented in the form of software, the invention may equally well be practiced in the form of a dedicated, full custom digital integrated circuit or, even in the form of an analog circuit, employing analog values as substitutes for the digital values disclosed in conjunction with the above specification.

In addition, while the preferred embodiment disclosed above takes the form of a pacemaker/cardioverter/defibrillator, the enhanced ability to distinguish between various tachyarrhythmias are also valuable and applicable to devices which are only capable of performing a subset of the various therapies discussed above in conjunction with FIG. 4. For example, the ability to distinguish between a fast ventricular tachycardia and ventricular fibrillation is valuable in an implantable cardioverter defibrillator, even if the cardiac pacing function is omitted, as in the currently available CPI AICD implantable cardioverter defibrillators. The ability to distinguish between VT and rapid rhythms due to atrial fibrillation is similarly of value in the context of an antitachycardia pacer, even in the absence of high energy cardioversion and defibrillation therapies. It should further be kept in mind that while the therapies described for delivery in response to detection of the various arrhythmias discussed are all disclosed in the context of electrical therapies, it is possible that the invention may be embodied in the form of an implantable drug dispenser, wherein one or more of the antitachycardia therapies takes the form of injection of a drug locally into the heart or systemically to treat the detected arrhythmia. As such, the above disclosure should be taken merely as an example of an embodiment of the present invention, rather than limiting, when reading the claims which follow.

In conjunction with above application, I claim:

1. Apparatus for treating tachyarrhythmias, comprising:
   treatment means for delivering a first therapy to a patient's heart to treat tachycardia and a second therapy to said patient's heart to treat fibrillation;
   first means for sensing electrical signals from said patient's heart indicative of the depolarization of a chamber or chambers of said patient's heart;
   means for measuring and storing the intervals separating said electrical signals:
   means for detecting the occurrence of a tachyarrhythmia; and
   tachycardia/fibrillation discriminator means responsive to said detecting means for selecting between said first and second therapies, said discriminator means in turn comprising:
   means for sorting said measured intervals into interval ranges;
   means for determining the numbers of intervals within each said interval range;
   means for identifying ones of said interval ranges which have the highest numbers of said stored intervals;
   means for determining the total number of said stored intervals falling within said identified interval ranges; and
   means for triggering said first therapy if said total number meets a predetermined criterion.

2. Apparatus according to claim 1 wherein said discriminator means further comprises means for triggering said second therapy if said total number fails to meet said predetermined criterion.

3. Apparatus according to claim 1 wherein said predetermined criterion comprises a threshold number of intervals and wherein said criterion is met if said total number of intervals meets or exceeds said threshold number.

4. Apparatus according to claim 1 wherein said first therapy comprises antitachycardia pacing.

5. Apparatus according to claim 1 wherein said first therapy comprises delivery of a cardioversion pulse.

6. Apparatus according to claim 2 wherein said second therapy comprises delivery of a defibrillation pulse.

7. A defibrillator, comprising:
   treatment means for delivering a therapy to a patient's heart to treat fibrillation;
   first means for sensing electrical signals from said patient's heart indicative of the depolarization of a chamber or chambers of said patient's heart;
   means for measuring and storing the intervals separating said electrical signals:
   means for detecting the occurrence of an arrhythmia; and
   discriminator means responsive to said detecting means for triggering said therapy, said discriminator means in turn comprising:
   means for sorting said measured intervals into interval ranges;
   means for determining the numbers of intervals within each said interval range;
   means for identifying ones of said interval ranges which have the highest numbers of said stored intervals;
   means for determining the total number of said stored intervals falling within said identified interval ranges; and
   means for identifying the occurrence of fibrillation and for triggering said therapy if said total number is less than a predetermined value.

8. Apparatus for treatment of tachycardia, comprising:
   treatment means for delivering a first therapy to a patient's heart to treat tachycardia;
   first means for sensing electrical signals from said patient's heart indicative of the depolarization of a chamber or chambers of said patient's heart;
   means for measuring and storing the intervals separating said electrical signals:
   means for detecting the occurrence of an arrhythmia; and
   discriminator means responsive to said detecting means for triggering said therapy, said discriminator means in turn comprising:
   means for sorting said measured intervals into interval ranges;
   means for determining the numbers of intervals within each said interval range;
   means for identifying ones of said interval ranges which have the highest numbers of said stored intervals;
   means for determining the total number of said stored intervals falling within said identified interval ranges; and
   means for identifying the occurrence of a tachycardia and for triggering said first therapy if said total number meets a predetermined criterion.

9. Apparatus according to claim 8 wherein said therapy comprises antitachycardia pacing.

10. Apparatus according to claim 8 wherein said first therapy comprises delivery of a cardioversion pulse.

11. Apparatus according to claim 8, further comprising:
    treatment means for delivering a second therapy to a patient's heart;
    means for triggering delivery of said second therapy if said total number fails to meet said predetermined criterion.

12. Apparatus according to claim 11 wherein said second therapy comprises delivery of a defibrillation pulse.

13. Apparatus according to claim 8, wherein said means for detecting the occurrence of an arrhythmia comprises means for detecting a tachycardia, further comprising:
- means for detecting the occurrence of fibrillation;
- treatment means for delivering a defibrillation pulse to a patient's heart to treat tachycardia; and
- means for inhibiting delivery of said first therapy if said total number fails to meet said predetermined criterion.

14. Apparatus according to claim 13 wherein said first therapy comprises antitachycardia pacing.

15. A tachycardia/fibrillation discriminator, comprising:
- means for sensing electrical signals from said patient's heart indicative of the depolarization of a chamber or chambers of said patient's heart;
- means for measuring and storing the intervals separating said electrical signals:
- means for detecting the occurrence of an arrhythmia; and
- means responsive to said detecting means for determining whether said detected arrhythmia is fibrillation or tachycardia, said responsive means in turn comprising:
- means for sorting said measured intervals into interval ranges;
- means for determining the numbers of intervals within each said interval range;
- means for identifying ones of said interval ranges which have the highest numbers of said stored intervals;
- means for determining the total number of said stored intervals falling within said identified interval ranges; and
- means for identifying tachycardia in response to said total number meeting a predetermined criterion and for identifying fibrillation in response to said total number failing to meet said predetermined criterion.

16. Apparatus for identifying an arrhythmia, comprising:
- means for sensing electrical signals from a patient's heart indicative of the depolarization of a chamber or chambers of said patient's heart;
- means for measuring and storing the intervals separating said electrical signals:
- means for detecting the occurrence of an arrhythmia; and
- means responsive to said detecting means for determining whether said detected arrhythmia is tachycardia or a rapid rhythm due to a different cause, said responsive means in turn comprising:
- means for sorting said measured intervals into interval ranges;
- means for determining the numbers of intervals within each said interval range;
- means for identifying ones of said interval ranges which have the highest numbers of said stored intervals;
- means for determining the total number of said stored intervals falling within said identified interval ranges; and
- means for identifying the occurrence of tachycardia in response to said total number meeting a predetermined criterion.

* * * * *